(12) United States Patent
Weber et al.

(10) Patent No.: US 9,414,950 B1
(45) Date of Patent: *Aug. 16, 2016

(54) REAR ENTRY ANKLE BRACE WITH MEDIAL AND LATERAL ACCESS

(71) Applicant: WEBER ORTHOPEDIC INC., Santa Paula, CA (US)

(72) Inventors: James J. Weber, Santa Barbara, CA (US); David Hsieh, Dongguan Guandong (CN); David Cormier, Oxnard, CA (US)

(73) Assignee: WEBER ORTHOPEDIC INC., Santa Paula, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,173

(22) Filed: Aug. 31, 2014

Related U.S. Application Data

(63) Continuation of application No. 13/908,959, filed on Jun. 3, 2013, now Pat. No. 8,821,427, which is a continuation-in-part of application No. 13/413,098, filed on Mar. 6, 2012, now Pat. No. 8,454,545, which is a continuation of application No. 13/364,236, filed on Feb. 1, 2012, now abandoned.

(60) Provisional application No. 61/439,115, filed on Feb. 3, 2011.

(51) Int. Cl.
*A61F 5/00* (2006.01)
*A61F 5/01* (2006.01)

(52) U.S. Cl.
CPC .................................. *A61F 5/0111* (2013.01)

(58) Field of Classification Search
CPC ... A61F 5/0109; A61F 5/0111; A61F 5/0102; A61F 5/0104; A61F 13/08; A61F 13/148; A61F 5/012; A61F 5/0127; A61F 13/061; A61F 13/496; A61F 13/55115; A61F 13/5655; A61F 2002/0852
USPC ...................................... 602/23–28; 128/882
See application file for complete search history.

(56) References Cited

U.S. PATENT DOCUMENTS

| | | | | |
|---|---|---|---|---|
| 8,484,545 | B2 * | 7/2013 | McLaughlin et al. | ......... 714/790 |
| 8,821,427 | B1 * | 9/2014 | Weber et al. | ..................... 602/23 |
| 2009/0247923 | A1 * | 10/2009 | Lundberg | ........................ 602/27 |

* cited by examiner

*Primary Examiner* — Michael Brown
(74) *Attorney, Agent, or Firm* — Paul Y. Feng; One LLP

(57) ABSTRACT

An ankle brace includes a foot and ankle holder made from a flexible fabric having a foot portion transitioning to an upper ankle portion with opposite first and second sides. The upper ankle portion has an open front and back. A rear portion is attached to partially enclose the open back. The rear portion has opposite first and second panels that removably attach to the first and second sides of the upper ankle portion, respectively. An optional tongue is located at the open front and laces overlie the tongue. A rigid heel support is disposed inside the foot portion, and the heel support may include pivoting joints. Elongated support straps extend under the foot portion and wrap around the ankle holder. Retention straps extend around the ankle holder.

16 Claims, 12 Drawing Sheets

REAR ENTRY ANKLE BRACE WITH MEDIAL AND LATERAL ACCESS

CROSS-REFERENCE TO RELATED APPLICATIONS

This application is a continuation of co-pending application Ser. No. 13/908,959, filed Jun. 3, 2013, which is a Continuation-In-Part of application Ser. No. 13/413,098, filed Mar. 6, 2012, now U.S. Pat. No. 8,454,545, which is a continuation of application Ser. No. 13/364,236, filed Feb. 1, 2012, now abandoned, which claims priority from U.S. Provisional Patent Application No. 61/439,115, filed Feb. 3, 2011, all of which contents are hereby incorporated by reference in their entirety.

FIELD OF THE INVENTION

This invention relates generally to ankle braces, and more particularly to improvements in such braces enabling ease and rapidity of application to the wearer's ankle.

BACKGROUND

Ankle sprains in the general population typically occur as a result of either excessive inversion or excessive eversion. An inversion ankle sprain is the internal rotation of the ankle joint; i.e., rolling the foot inward or medially, and overstretching and usually injuring the outer ligaments in the ankle. This accounts for about 90 percent of all ankle sprains. An eversion ankle sprain is the external rotation of the ankle joint; i.e., rolling the foot outward or laterally.

The ankle is an assembly of bones held together by a number of soft tissues such as muscles, ligaments, tendons, and cartilage. In the typical ankle injury, a traumatic impact or force causes the foot to invert or evert relative to the lower leg. When the off-centered force induces inversion or eversion of the foot relative to the lower leg in excess of the natural limits of the soft tissue structures, that soft tissue is damaged. The injury may include stretching or tearing of the soft tissues and, if severe enough, damage or fracture to the bones in the ankle joint, lower leg, and foot.

Ankle braces and supports are prescribed as a treatment for an ankle sprain or fracture, or to prevent further injury to the weakened joint. It should support and stabilize the ankle and foot to limit inversion and eversion, but should not overly limit the flexion motions associated with the foot motions of the wearer walking, running, lunging, pivoting, etc. If the injured ankle is substantially immobilized by the ankle brace, rehabilitation is delayed and a stiff ankle may result, which opens the possibility for re-injury.

Injuries to ankles typically require the application of ankle braces, which must be repeatedly applied and removed at short intervals during the rehabilitation period. Thus, ease and rapidity of application and removal are important to the wearer. The ankle brace cannot be complicated so that it is easy for the wearer to physically put on and take off, and should also be comfortable to wear.

SUMMARY OF THE INVENTION

An ankle brace with medial-, lateral-, or rear-entry access by the wearer into and out of the brace, comprising a foot and ankle holder preferably made from a sheet of soft fabric without a rigid frame or skeleton, defined by a foot portion transitioning to an upper ankle portion with opposed first and second sides, wherein the upper ankle portion includes an open back and an open front. A rear portion or posterior panel discrete from the foot and ankle holder removably attaches to the upper ankle portion to at least partially enclose the open back. In the preferred embodiment, the rear portion or posterior panel includes opposed first and second panels that, independently, removably attach to the first and second sides, respectively, of the upper ankle portion. An optional padded tongue is located at the open front of the ankle holder. Means for binding is provided, overlying the tongue, to bind the first and second sides of the upper ankle portion together. At least one elongated support strap is connected to the ankle holder and extends under the foot portion and then extends generally upwardly and rearwardly for removable retention to at least one of the first and second sides.

At least one retention strap, preferably including an elastic material, is connected to the holder, and extends around the holder to at least partially overlie and to removably connect to the support strap. Accordingly, one of the first and second panels may be independently detached from the respective first and second sides of the upper ankle portion for lateral, medial, and rear access by the wearer into and out of the ankle brace, via the open back of the foot and ankle holder. As such, the means for binding, preferably a lacing system, does not need to be untied (after the initial adjustment) so that the wearer can conveniently and quickly withdraw his or her foot from ankle brace. The same for wearing the ankle brace—the tied lacing system does not need to be undone, adjusted, and tied again for the wearer to insert his or her foot back into the ankle brace and return to normal activity. The is highly attractive feature to athletes, the elderly, those with limited mobility or range of movement.

The means for binding the first and second sides of the upper ankle portion together may be a system of laces and eyelets or loops, straps, buttons, snaps, zippers, latches, hooks, hook-and-loop fasteners (Velcro), and the like, or any combination thereof.

The ankle brace optionally includes a rigid heel support disposed at the foot portion. In a preferred embodiment, the rigid heel support is a U-shaped strip that extends from the medial side, underneath the heel, to the lateral side. The rigid heel support strip is stitched, cemented, or sewn onto or into the foot portion and supports the wearer's heel in a stirrup fashion. In an alternative embodiment, the rigid heel support is made from multiple pieces joined by pivots to accommodate ankle movement.

DETAILED DESCRIPTION OF THE PREFERRED EMBODIMENTS

Figure 1:
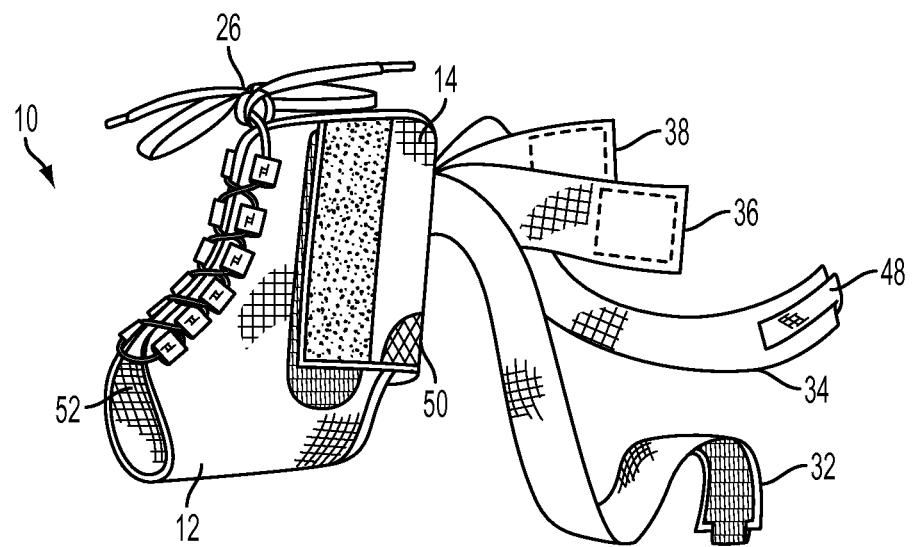
FIG. 1 is a side elevational view of a preferred embodiment rear entry ankle brace with medial and lateral access.

FIG. 1 is a side elevational view of a preferred embodiment stabilizing ankle orthosis, support, or brace 10 for prophylactic and chronic sprains. The exemplary ankle brace 10 limits inversion/eversion while not restricting plantar and dorsiflexion. The ankle brace 10 is a rear-, medial-, or lateral-entry design, and in the preferred embodiment, is constructed preferably from a foot and ankle holder 12 and a separate, detachable rear portion or posterior panel 14.

The foot and ankle holder 12 and the rear portion 14 are preferably made from one or more thin layers or sheets of a soft and flexible fabric. The fabric may be ballistic nylon, spacer fabric, durable mesh knit nylon, suede, leather, denim, or vinyl, or any combination thereof or like materials. In the preferred embodiment, the fabric of the foot and ankle holder 12 and rear portion 14 do not have any internal or external rigid supports or skeleton. Accordingly, the foot and ankle holder 12 with the attached rear portion 14 is highly flexible and is generally shapeless when not being worn, similar to a crumpled bath towel. This flexibility gives the wearer tremendous comfort and joint mobility, especially prized by an athlete. The lack of rigid internal or external supports also reduces the overall weight of the ankle brace 10, another important consideration for the athlete.

Figure 2:
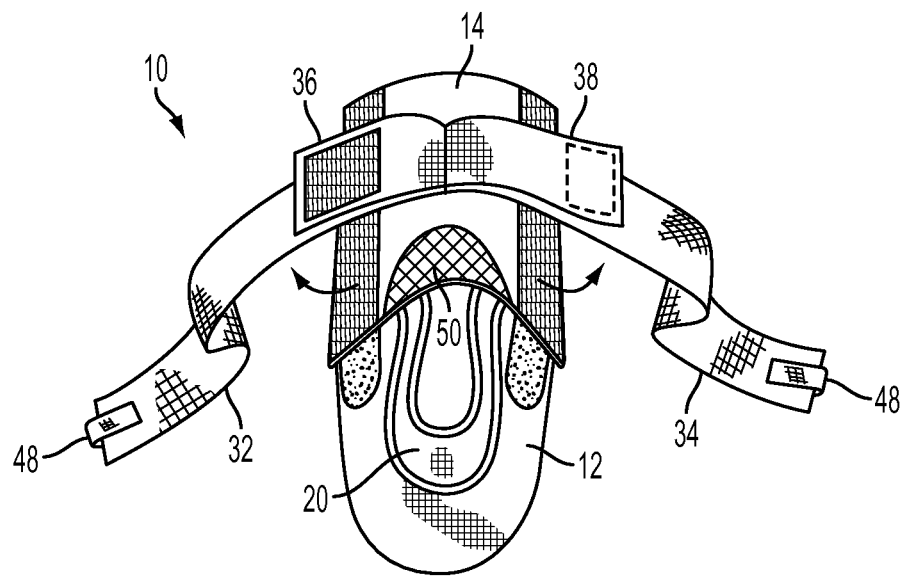
FIG. 2 is a rear or posterior view of the ankle brace of FIG. 1.

FIG. 2 is a rear elevational view of the ankle brace 10 showing the foot and ankle holder 12 attached to the rear portion 14. In the preferred embodiment, the side panels/sides 28, 30 of the rear portion 14 at least partially overlap, and independently attach to and detach from the respective side panels 22, 24 of the foot and ankle holder 12 via, preferably, hook and loop fastener patches. This feature is indicated by the arrows in FIG. 2.

Figure 3:
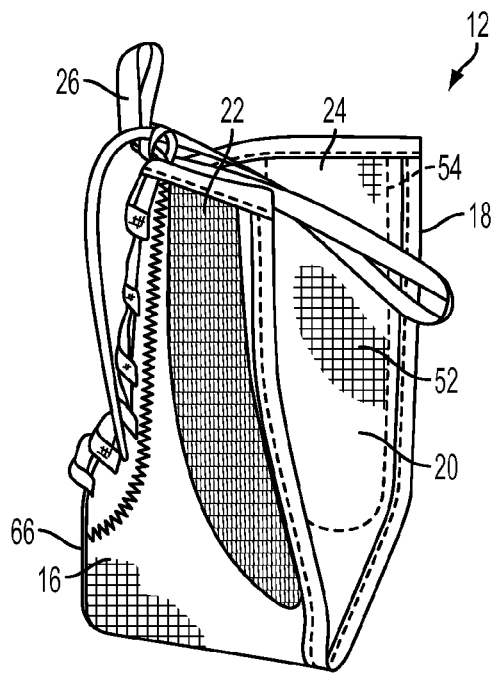
FIG. 3 is a side elevational view of the foot and ankle holder of the ankle brace from FIG. 1.
Figure 4:
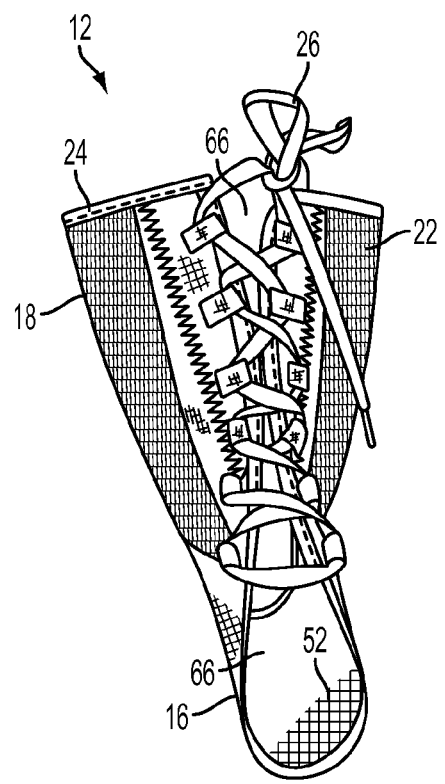
FIG. 4 is a front or anterior elevational view of the foot and ankle holder of FIG. 3.

FIG. 3 is a side elevational view of the preferred embodiment foot and ankle holder 12 only, and FIG. 4 is a front elevational view of the foot and ankle holder 12 only. The foot and ankle holder 12 has a foot portion 16 that transitions into an upper ankle portion 18. As seen in FIG. 2, the sole area of the foot portion 16 is preferably seamless to reduce irritation under the wearer's foot. Also in FIG. 2, the rear portion 14 optionally includes a soft patch 50 to gently engage the Achilles tendon of the wearer.

As best seen in FIG. 3, the foot and ankle holder 12 has an open posterior area or open back 20 that enables the wearer to insert his or her foot into the brace 10. The open back 20 further provides a large heel opening for the wearer's comfort.

The foot and ankle holder 12 has opposed first and second side panels or sides 22, 24. As seen in the front view of FIG. 4, the foot and ankle holder 12 also has an open anterior or front 66 where the wearer's forefoot and toes protrude from the foot portion 16. The upper areas of the open front 66 as seen in FIG. 4 can be pulled together by the wearer tightening the means for binding 26, here cinching the laces and tying a knot as shown. Thus, the anterior or front edge of the sides 22, 24 are bound and held together by the means for binding 26. In various alternative embodiments, the means for binding 26 may be laces as shown, or may be a wire strand, straps, buttons, snaps, zippers, hooks, claws, hook-and-loop (Velcro) fasteners or patches, and the like, or any combination thereof. As shown in FIGS. 3 and 4, the laces 26 pass through speed loops or optional eyelets at the front of the foot and ankle holder 12 that can be easily cinched and then tied at the top as shown.

In the preferred embodiment, the foot and ankle holder 12 does not require a tongue residing underneath the laces 26 where the front leading edges of the first and second sides 22, 24 meet, as in FIG. 4. The underside interior of the front portion of the foot and ankle holder 12 beneath the laces may be padded. The front leading edges of the foot and ankle holder 12 are pulled together and closed by the tightened laces 26. The laces 26 do not directly press against the wearer's foot so the tongue is unnecessary. The present invention design thus proceeds against conventional wisdom of having a tongue in an ankle brace.

Omitting a tongue simplifies construction and simplifies the procedure for the wearer when putting on or taking off the ankle brace 10; attaching the brace and removing the brace are accomplished quickly. This is advantageous to athletes and those who have daily exercise-related routines requiring that the ankle brace be worn and removed frequently. No tongue also means no shifting of internal parts that touch the wearer's foot during use, which may be uncomfortable or a nuisance to adjust.

Figure 5:
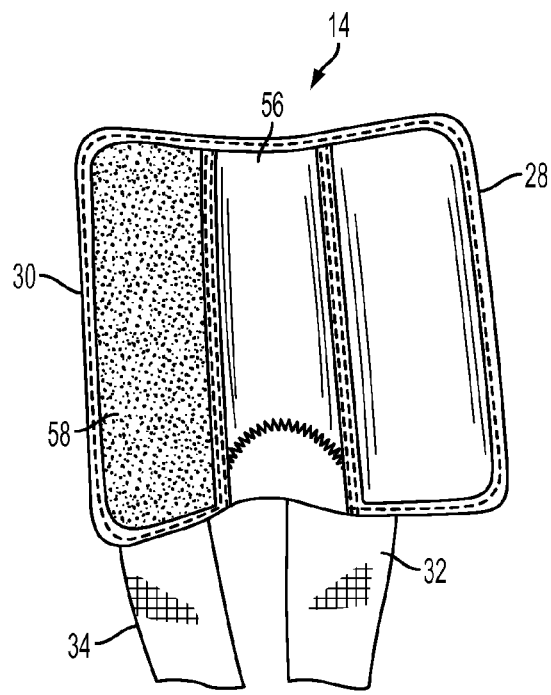
FIG. 5 is an internal view of the rear portion of the ankle brace from FIG. 1.
Figure 6:
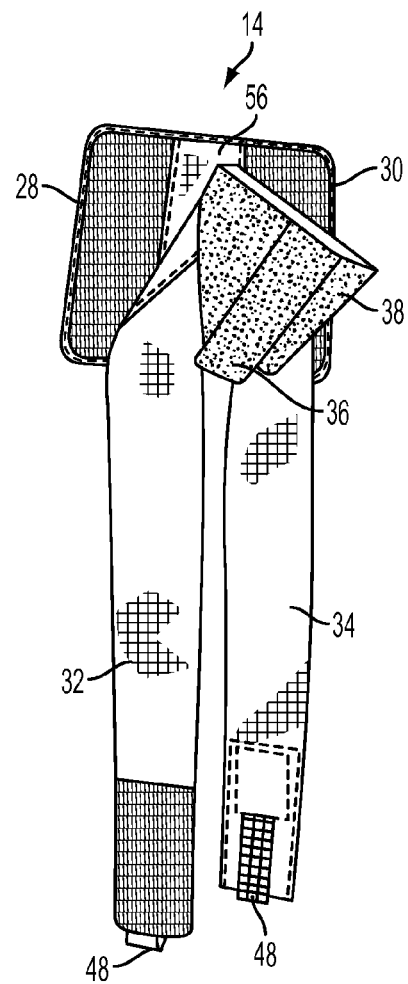
FIG. 6 is a back, exterior view of the rear portion of the ankle brace, showing the entire length of the elongated support straps.

FIGS. 5 and 6 are various isolated views of the detachable rear portion or posterior panel 14, shown attached to the foot and ankle holder 12 in FIGS. 1 and 2. Rear portion 14 has opposite first and second panels 28, 30 extending from a middle portion 56. FIG. 5 is an interior view of the detached rear portion 14 showing the surface that engages the wearer's lower calf and Achilles area. Complementary portions of hook-and-loop fasteners 58 may be applied to the interior of the first and second panels 28, 30 for attachment to the exterior sides 22, 24 of the foot and ankle holder 12 as illustrated in FIG. 1. Overall, the rear portion 14 is preferably made from one or more thin layers or sheets of flexible fabric. FIG. 6 is an exterior view of the rear portion 14. As best seen in FIG. 6, there are preferably two elongated support straps 32, 34 attached to the exterior surface of the rear portion 14. There may be fewer or more support straps.

The elongated support straps 32, 34, preferably two of them, made from inelastic nylon or high strength webbing, are used to wrap and compress the wearer's foot and ankle area. Each strap 32, 34 circumscribes the ankle and the midfoot area in opposite directions. The long support straps 32, 34 give the wearer the option to wrap with multiple turns the specific area of the ankle that requires the greatest amount of support.

As seen in FIG. 6, also attached to the rear portion 14 are a pair of retention straps 36, 38. The retention straps 36, 38 include an elastic material. The retention straps 36, 38 are shorter than the support straps 32, 34 and are not meant to circumscribe the wearer's foot of ankle as with the support straps. Rather, the retention straps 36, 38 are stretched and attached to the lateral and medial sides of the foot and ankle holder 12 using hook and loop fasteners. The oppositely extending straps 36, 38, applying circumferential tension as with a cuff, help secure the ankle brace 10 to the wearer while minimize shifting or slippage even during physical activity by the wearer.

Figure 7:
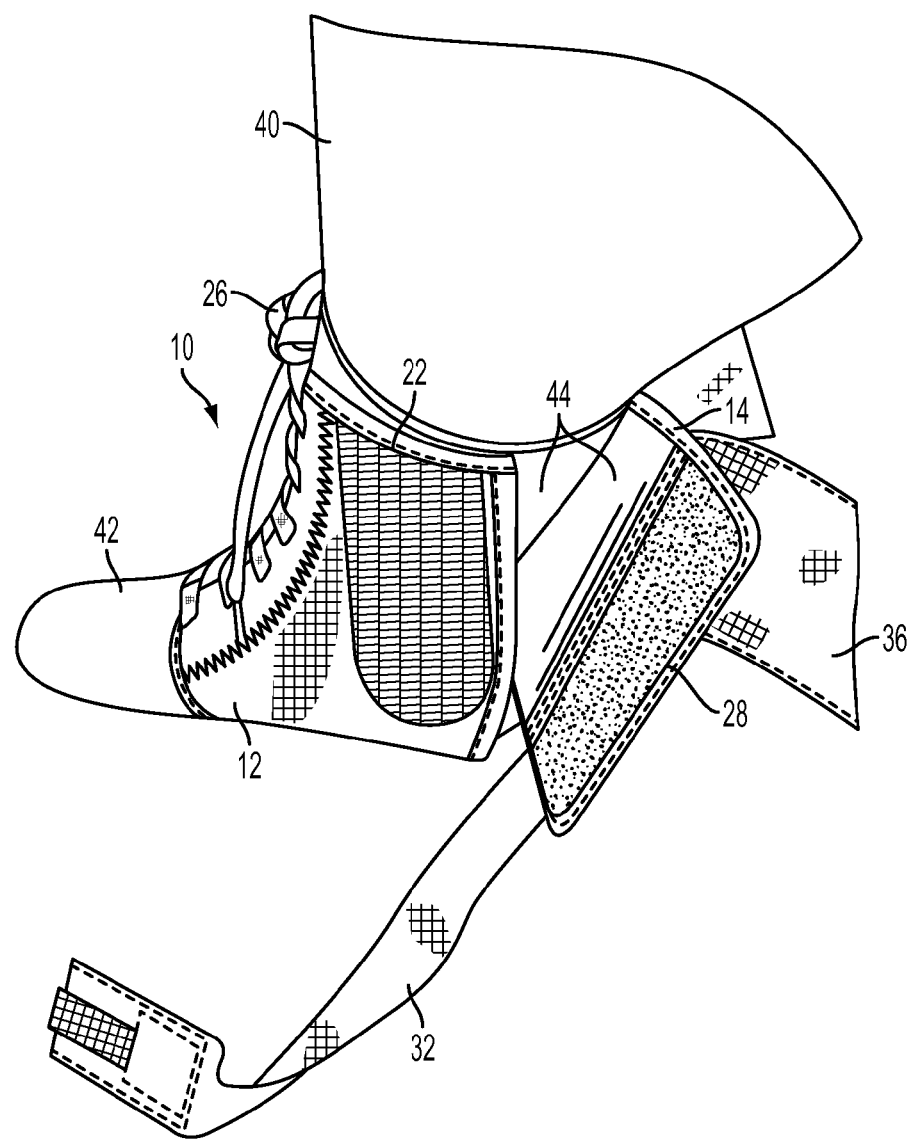
FIG. 7 shows a first flap of the rear portion in an open position, with the ankle brace worn on the right foot, allowing entry into the ankle brace from the medial side of the right foot.

FIG. 7 is a perspective view seen from the medial side of the ankle brace 10 as applied to a wearer's right leg 40. The ankle brace 10 also partially covers the wearer's right foot 42 allowing the forefoot and toes to extend out into the open. The wearer is shown optionally wearing a sock. The foot and ankle holder 12 generally wraps over the front and side portions of the ankle, midfoot, and lower leg, while the rear portion 14 covers the rear portion of the wearer's ankle and lower leg, and overlaps with the foot and ankle holder 12 at the sides 22, 24. As seen in FIG. 7, the wearer has already threaded, adjusted, tightened, and tied the means for binding 26. Also at this stage, the elongated support straps 32, 34 have not been applied or have been removed. Likewise, the retention straps 36, 38 have not been applied or have been released.

A medial side opening 44 in the ankle brace 10 is created when the first panel 28 is independently detached from the first side of the ankle holder 12—independently detached because, although hidden from view in FIG. 7, the lateral side of the wearer's right leg 40 is still covered by the foot and ankle holder 12. As such, the second side 24 remains attached to the second panel portion 30 of the foot and ankle holder 12. This connection maintains structural support of the ankle brace 10 even though the medial side is opened as shown. The support and retention straps 32, 34, 36, 38 still in place ensure that the ankle brace 10 does not accidentally slide or fall off of the wearer's foot, making the putting-on-taking-off routine complicated for the wearer. Consequently, the opening 44 enables the wearer to insert or remove his or her right foot 42 into or out of, respectively, the ankle brace 10 from the medial side.

Beneficially, this same ankle brace 10 can be worn on the left foot, although not shown. Similar as seen to FIG. 7, if worn on the left foot, a space 46 can be created by lifting the second panel 30 and moving it away from the second side 24 of the foot and ankle holder 12 thus allowing the wearer to remove her foot or insert her foot into or out of the ankle brace 10 from the medial side for the left foot.

Figure 8:
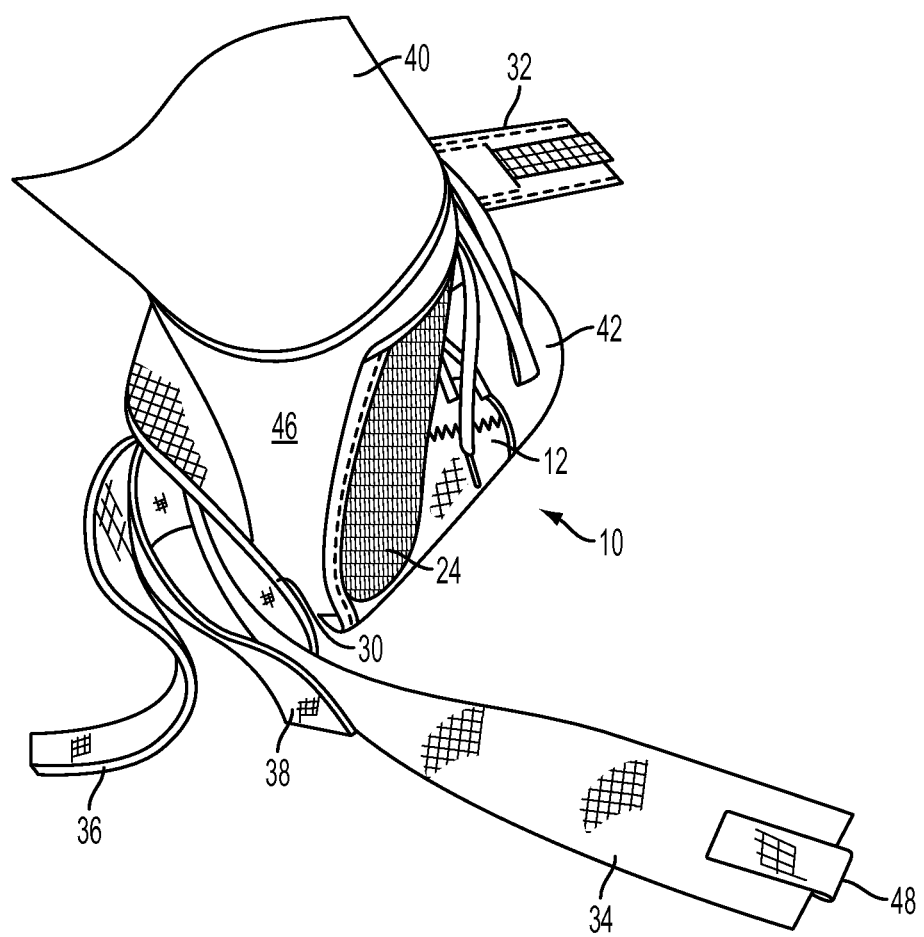
FIG. 8 shows a second flap of the rear portion in an open position, with the ankle brace worn on the right foot, allowing entry into the ankle brace from the lateral side of the right foot.

FIG. 8 shows the ankle brace 10 partially applied to the wearer's right leg 40. Looking at the lateral side of the right leg 40 in this view, it can be seen that when the second panel 30 is detached from the second side 24, a lateral opening 46 is created allowing the wearer to insert or withdraw his or her foot 42 into or out of the ankle brace 10. The medial side of the ankle brace 10 has the first side 22 of the holder 12 still attached to the first panel 28 of the rear portion 14 thus giving structural support to the ankle brace 10 even though opening 46 is created. In the FIG. 8 view, the elongated support straps 32, 34 and retention straps 36, 38, are not yet in use and not bound.

Figure 9:
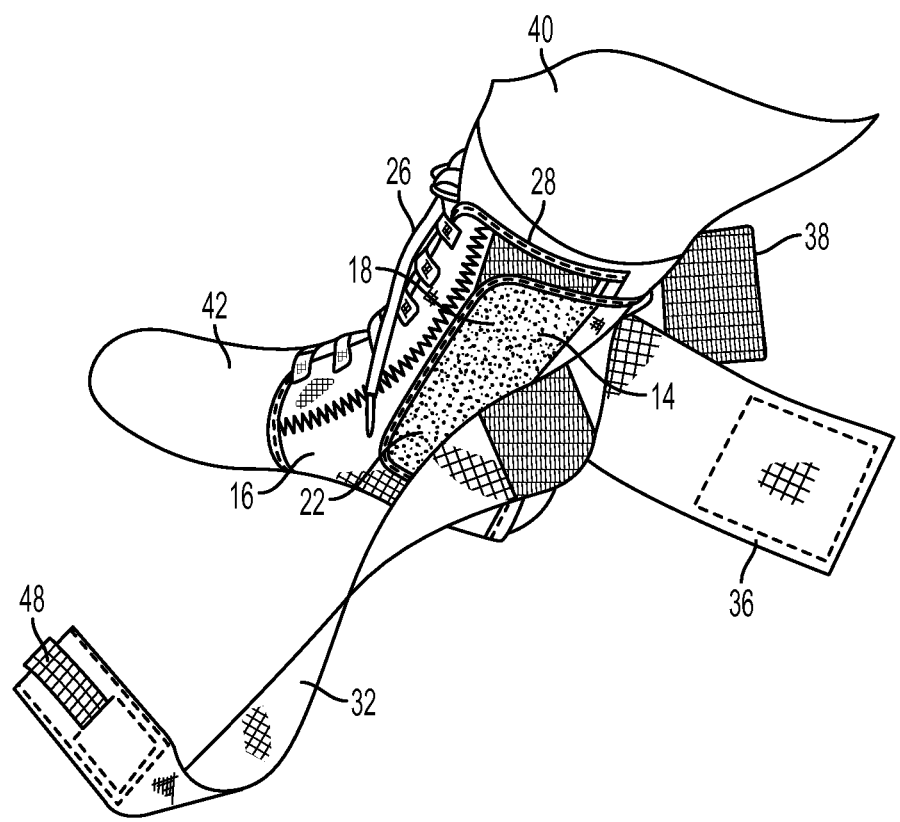
FIG. 9 is a perspective view showing the ankle brace of FIG. 1 worn on the right foot, with the rear portion attached to the foot and ankle holder, and the straps just prior to applying them to the ankle brace.

FIG. 9 shows the rear portion 14 attached to the foot and ankle holder 12 on both the medial and lateral sides. Again the ankle brace 10 is shown worn on the right leg 40. With the holder 12 and rear portion 14 attached together, the means for binding (preferably laces) 26 may be further cinched up and tied for a precise fit. Alternatively, the overlapping side panel attachments 22, 24, 28, 20 of the foot and ankle holder 12 and the rear portion 14 may be adjusted relative to each other, thus making fitment of the brace 10 looser or tighter for the wearer. If desired, the overlapping side panels 22, 24, 28, 30 allow for gross adjustment of the fitment, and the laces allow for more precise adjustment of the fitment on the patient.

Next, the wearer takes each support strap 32, 34 starting on one side at the back of the ankle, then passes it by or circumscribes the ankle at about the malleoli, then proceeds underneath the midfoot and sole, and may wrap over the instep, then extends upward to the opposite side of the ankle, and finally attaches the end to the upper ankle portion 18. The second strap is applied in the opposite direction. The wrapping description is only provided here to illustrate a use of the present invention ankle brace; the exact technique will be given to the patient by the treating physician, orthopedist, or physical therapist. Once applied, the straps 32, 34 help support and stabilize the ankle for treatment of ankle sprains, post injury rehabilitation, etc.

The wearer then applies the elastic retention straps 36, 38. The retention straps 36, 38 are pulled forward and stretched, then locked down by hook and loop fasteners, claw hooks, etc. at or near the ends. The retention straps 36, 38 are thicker than the inelastic support straps 32, 34, and wrap around the lower leg just above the malleoli, and overlie the retention straps 36, 38. Aside from keeping the ankle brace 10 in place on the wearer's ankle and foot, the elastic retention straps 36, 38 act as a cuff compressing and stabilizing this area, and improving the support for the ankle joint.

Figure 10:
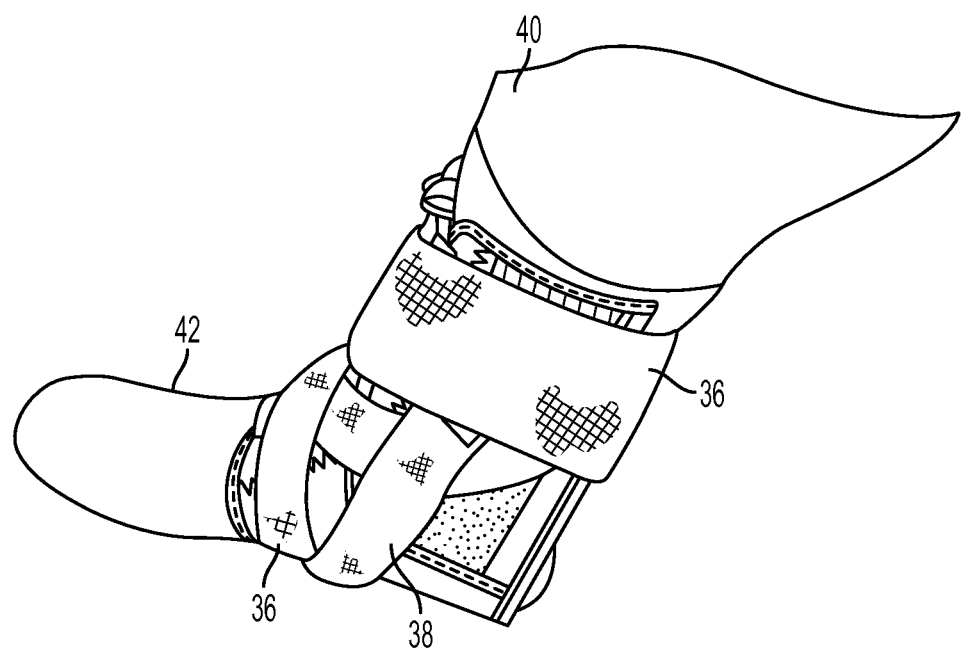
FIG. 10 is a perspective view showing the ankle brace of FIG. 9 worn on the right foot, with the rear portion attached to the foot and ankle holder, and the straps wrapped around the foot and ankle and attached to the brace.

FIG. 10 shows the ankle brace 10 worn on the right leg 40 with all of the straps in place. FIGS. 9 and 10 show the ankle brace 10 worn on the wearer's right leg 40 and provide a medial point of view. The ankle brace 10 may likewise be worn on the left foot, although not shown. FIGS. 7-10 thus show that when the ankle brace 10 is worn on the wearer's right leg, it is possible to access the ankle brace 10 medially as seen in FIG. 7 or laterally as seen in FIG. 8. Similarly, if the ankle brace 10 is worn on the left leg, medial and lateral access to the ankle brace 10 are likewise possible.

Another advantage with the medial and lateral access via the overlapping side panels 22, 24, 28, 30 is that the wearer does not need to work with the laces 26. Oftentimes, a more obese or elderly patient might not have the range of motion or reach to access the laces to cinch them down, and to tie or untie them. Sometimes, the patient will not be able to bend over to apply a conventional ankle brace or remove it from his ankle. On the other hand, with the present invention ankle brace 10, the patient can cross his left or right leg with the injured ankle while seated comfortably on a chair, then open the medial side of the ankle brace, and insert his foot through the medial opening 44. Removing the ankle brace 10 involves the same procedure; sitting in a chair, crossing the leg with the injured ankle, detaching the medial panel from the foot and ankle holder to reveal the medial opening 44, and withdrawing the foot from the brace. The patient also has easy access to the support and retention straps while in the seated, leg crossed position. Therefore, the medial and lateral access of the present invention ankle brace alleviates hardship for many wearers who lack range of motion.

For athletes and highly active individuals who have an ankle injury, the overlapping side panel access gives the wearer much quicker on or off capability than tying and untying the laces in the front, which becomes a chore if performed frequently. To be sure, once the laces 26 are adjusted, cinched up and tied, they do not need to be untied to release the foot from the ankle brace 10. Rather, the wearer simply detaches either the medial or lateral retention strap 36, 38, then detaches either the first or the second side panel 28, 30 from the foot and ankle holder 12 and pulls his foot out from the medial opening 44 or the lateral opening 46. The entire rear portion 14 can also swing fully open as in a car door so the wearer can withdraw his foot directly rearward. When the wearer returns to using the ankle brace again, he simply inserts his foot through the rear, medial or lateral openings 20, 44, 46, swings the rear portion 14 to close whichever opening 20, 44, 46, and reattaches the side panel 28, 30 to the side or sides 22, 24 of the foot and ankle holder 12. The detached retention strap 36, 38 is now stretched and reattached, and the ankle brace 10 is in position and ready. Furthermore, in the foregoing process, the support straps 32, 34, depending on how they are wrapped around the wearer's ankle brace 10, do not necessarily have to be disturbed or removed from their wrapped and bound state. This makes the ankle brace on or off procedure ever faster and easier.

Retention straps 36, 38 are preferably elastic and include Velcro fasteners at the ends. The retention straps 36, 38 are stretched by the wearer and then locked down by attachment of the Velcro fasteners to the exterior surfaces of the rear portion 14. The elasticity in straps 36, 38 apply a compressive force to the lower leg area. The elongated support straps 32, 34 may be elastic, but is preferably inelastic, and similarly have Velcro patches at the very ends to attach to the exterior of the foot and ankle holder 12 or the rear portion 14. As seen in FIGS. 1 and 2, optional finger loops 48 may be provided at the ends to allow the wearer for easier gripping and tightening of the elongated support straps 32, 34.

On advantage is the present invention ankle brace 10 may be worn on either the left or right foot without requiring two mirror image configurations be stocked by the orthopedic supplier. This saves a lot of money in terms of inventory costs and storage space. Further, regardless of which leg the ankle brace 10 is worn on, the wearer can insert or remove his or her foot into or out of the ankle brace 10 from the medial side, the lateral side, or from the rear of the brace by flipping open one or more of the side panels 28, 30 of the rear portion 14.

The ankle brace 10 has a low profile design as seen in FIG. 10, which enables an easy fit in athletic shoes, work boots, and the like. The low profile design further allows the user to wear athletic socks, work socks, or stockings, yet still fit within his or her everyday shoes. The large opening 20 in the back of the ankle brace (FIG. 2) permits the heel to protrude, which improves wearer comfort.

Figure 11:
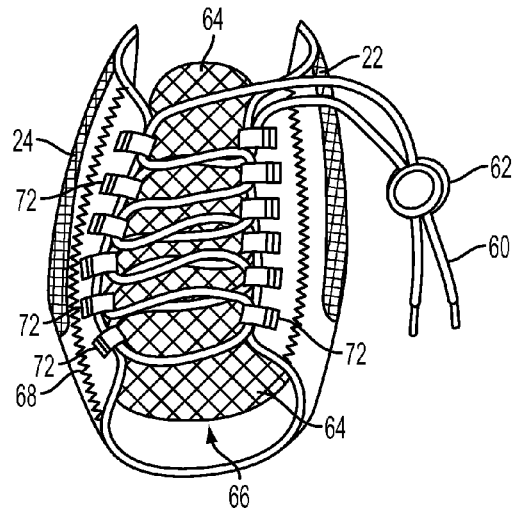
FIG. 11 is a front view of an alternative embodiment foot and ankle holder with a tongue and a speed lace.

FIG. 11 is a front view of an alternative embodiment foot and ankle holder 68. The ankle holder 68 has a front or anterior opening 66 that includes a tongue 64 stitched at its sides to the foot and ankle holder 12. The tongue 64 is made from a stretchable, padded material. Some patients have a wider foot, and use of the tongue 64 in the ankle brace thus accommodates those wider sized feet. Also, the means for binding in this embodiment includes a wire strand 60 and shoe lace loops 72. The wire strand speed lace 60 is a thin cord with a circular cross-section. Because of its thin diameter, the lace can be cinched through the shoe lace loops 72 faster because of less drag against the loops. A pushbutton, spring-based clamp 62 locks the ends of the speed lace 60 together in lieu of a knot to maintain tension.

Figure 12A:
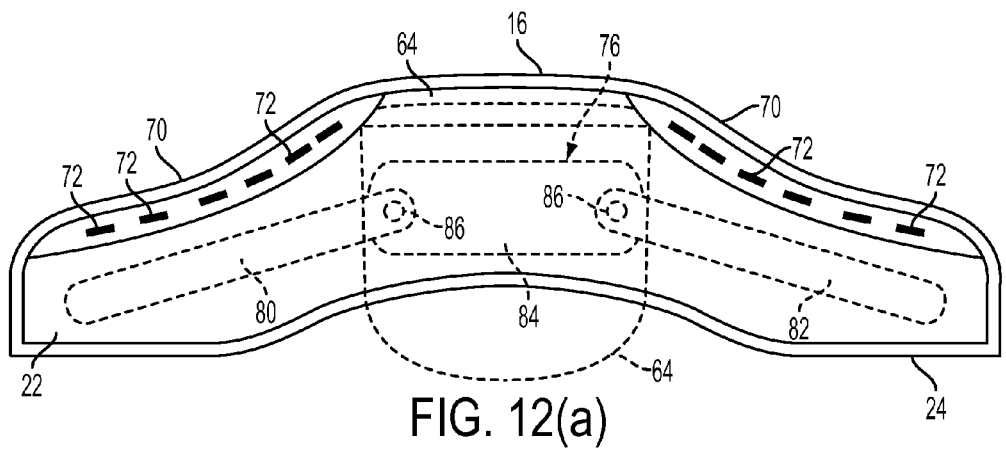
FIG. 12(a) shows an alternative embodiment foot and ankle holder with a rigid heel support with pivots embedded in the foot portion of the foot and ankle holder.
Figure 12B:
FIG. 12(b) shows an alternative embodiment rigid heel support without pivots.
Figure 12C:
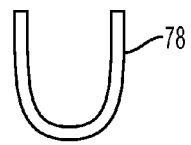
FIG. 12(c) is an end view of the rigid heel support of FIG. 12(b).

FIG. 12(*a*) shows an alternative embodiment foot and ankle holder 70. The shoe laces and foot portion have been removed, and the foot and ankle holder 70 has been laid open to reveal the interior. The foot portion 16 is at the center and the first and second sides/side panels 22, 24 are spread apart. The top of the foot and ankle holder 70 depicted in FIG. 12(*a*) is the front/anterior while the bottom is the posterior/back. For clarity of the illustration, the tongue 64 is depicted in phantom/dashed lines and has been folded and flipped downward from its normal position, which is flipped up and located adjacent the binding means 72. The binding means 72 in this embodiment are loops 72 and laces 60 shown in FIG. 11. Of course, shoe lace eyelets can be used in place of loops 72.

In the FIG. 12(*a*) embodiment, the soft fabric of the foot and ankle holder 70 has been reinforced with a rigid heel support 76, shown in dashed lines. The rigid heel support 76 is laid flat and inserted into the foot portion 16. By this arrangement, when the present invention foot brace is worn, the rigid heel support 76 acts as a stirrup supporting the wearer's heel while the heel support is situated inside the shoe, sneaker, or boot. The rigid heel support 76 when laid out has a thin rectangular strip shape as shown, and may optionally be made in multiple segments or pieces so that the discrete segments 80, 82 are connected to the main portion 84 with pivots 86. These segments 80, 82 may further extend into the upper sides 22, 24 of the foot and ankle holder 70. The segments 80, 82 function as side walls supporting and stabilizing the medial and lateral sides of the ankle, and the segments 80, 82 may extend up to and include the medial and lateral malleoli. The pivots 86 allow the rigid heel support 76 to flex along with the wearer's ankle during physical activity.

FIG. 12(*b*) shows an alternative embodiment rigid heel support 78 that is made from a thin, flat, continuous strip of rigid plastic. It is polymer molded to preferably have a free-standing U-shape, as seen from an end view in FIG. 12(*c*). Once inserted into the foot and ankle holder 70 of FIG. 12(*a*), the molded U-shape tends to flex the fabric of the foot portion 16 and sides 22, 24 into a U-shape to partially surround the wearer's heel as in a stirrup.

The plastics used for the rigid heel support is preferably HDPE or nylon, and other materials such as aluminum and rubber are contemplated. Such materials have the rigidity and strength even in a thin strip form to sufficiently stabilize an injured ankle, but are still lightweight so as to easily fit inside an athletic shoe without impeding comfort or mobility. The pivots 86 can be a simple hinge, such as a boss or hook on one piece fitted into a receiving hole on another piece; or a rivet or a pin that enables the segments 82 to swivel independently from the main portion 84. The rigid heel support 76, 78 can be inserted into a pocket inside the fabric foot and ankle holder so that it can be removed by the user as an option, stitched or sewn to a surface of the fabric, cemented to a surface of the fabric, permanently embedded within the fabric as shown, or the like.

In various alternative embodiments, the foot and ankle holder 12 and/or the rear portion 14 is made from a non-stretchable cotton fabric. Heavy gauge ballistic nylon, non-stretchable nylon fabric, cotton velour, or the like, may be used in alternative embodiments, and each of the materials may be used individually or in combination. The expanse of cotton fabric may be further reinforced with cross-stitched thread 52 (indicated by partial cross-hatching in the drawings). Padding may be inserted into key locations of the foot and ankle holder 12 and the rear portion 12 to improve comfort. Optional semi-rigid inserts or stays can be placed inside optional medial or lateral pockets 54 in key areas such as side panels 22, 24 of the holder 12, or in the panels 28, 30 of rear portion 14, to increase stability and support for the ankle. The stays may be stackable inside a pocket for extra rigidity and support. The stiffeners can be made of aluminum, steel, or plastic material that conforms to the shape of the ankle surface.

In still other alternative embodiments, the retention straps 36, 38 are made from non-stretchable, non-fraying nylon. The retention straps 36, 38 may be made from an elastic material such as Neoprene, rubber, etc.

FIGS. 13-18 show alternative embodiments of the ankle brace disclosed above, including adding a secondary closure, using complementary first and second attachment means to fasten the respective side panels of the foot and ankle holder to the rear portion, and the addition of a foot plate.

Figure 13:
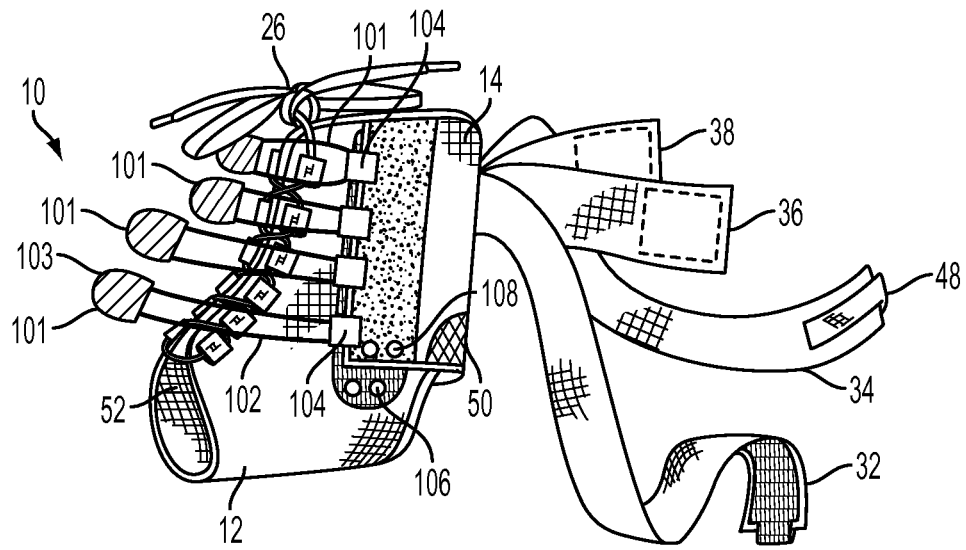
FIG. 13 is an alternative embodiment ankle brace with a secondary closure attached to the anterior of the ankle brace.
Figure 14:
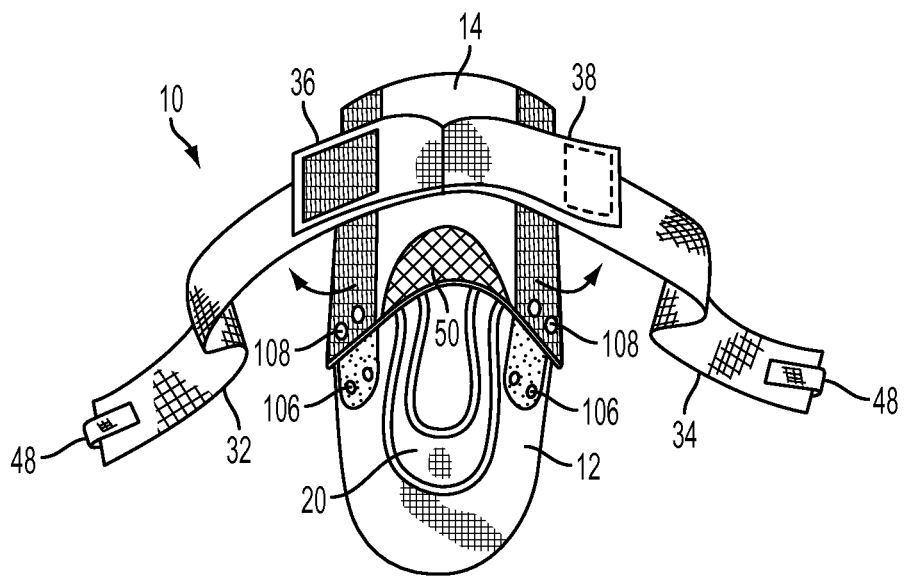
FIG. 14 shows an alternative embodiment ankle brace with the first and second complementary attachment means.
Figure 16:
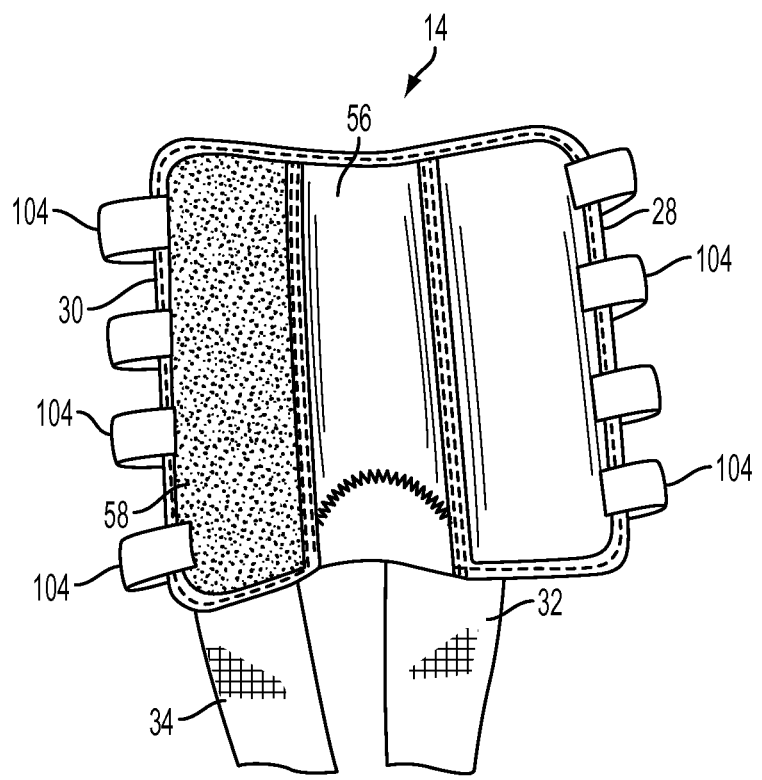
FIG. 16 shows an alternative embodiment ankle brace with lace loops for the secondary closure.

FIG. 13 shows the ankle brace 10 described above with a secondary closure 101. The secondary closure 101 in the preferred embodiment has a plurality of wire, string, rope, or like laces 102 terminating at attachment pads 103. The laces 102 are threaded through lace loops 104 formed in or stitched to the rear portion 14, as seen in FIG. 16. As preferably fitted to the ankle brace 10, the laces 102 are threaded through the loops 104 in the rear portion 14 and overlie the open front 66 and are anchored to the first and second panels 28, 30 of the rear portion 14 by attachment pads 103 that have hook and loop fasteners thereon. The laces 102 also preferably overlie the means for binding 26 the foot and ankle holder 12. The laces 102 may be short in length as shown in FIG. 13 so that they only wrap partially across the front of the ankle brace and anchor to the panel 28, 30 opposite to the panel having the lace loops 104; or the laces may be very long to circumscribe most of the ankle brace and attached to the same panel as the lace loops 104. In various alternative embodiments, the laces may have attachment panels at opposite ends so the lace loops may be omitted, or the laces and loops are used in combination where the laces are threaded back and forth through the loops and the ends of the laces have attachment pads for anchoring to the first and second panels 28, 30.

FIG. 13 also depict first and second complementary attachment means 106, 108 that are disposed on the side panels 22, 24 of the foot and ankle holder 12 and the side panels 28, 30 of the rear portion 14. The first and second complementary attachment means 106, 108 may be pushbutton button snaps, zippers, rivets, screws, hooks and D-rings, hook and loop fasteners, eyelets and laces, and like fasteners known in the art. The preferred embodiment ankle brace has a plurality of complementary attachment means 106, 108 disposed on the side panels 22, 24, 28, 30 so there is adjustability in the attachment points. If snaps are used, for example, the attachment of the rear portion 14 to the foot and ankle hold 12 is performed by the patient by aligning one or more pushbutton snaps with the respective bosses while adjusting the fitment. Once this is done, the patient has custom fit the brace to his or her ankle. Furthermore, the ankle brace may then be removed from the medial or lateral side while the snaps on the opposite side remain attached so that the brace may be reapplied to the ankle without further adjustment by the patient to the unopened side. The first and second complementary attachment means 106, 108 further bolster the relative positions of the foot and ankle holder 12 to the rear portion 14 when worn for more vigorous activity, for example, so there is less likelihood of the two components shifting or detaching from each other.

Figure 15:
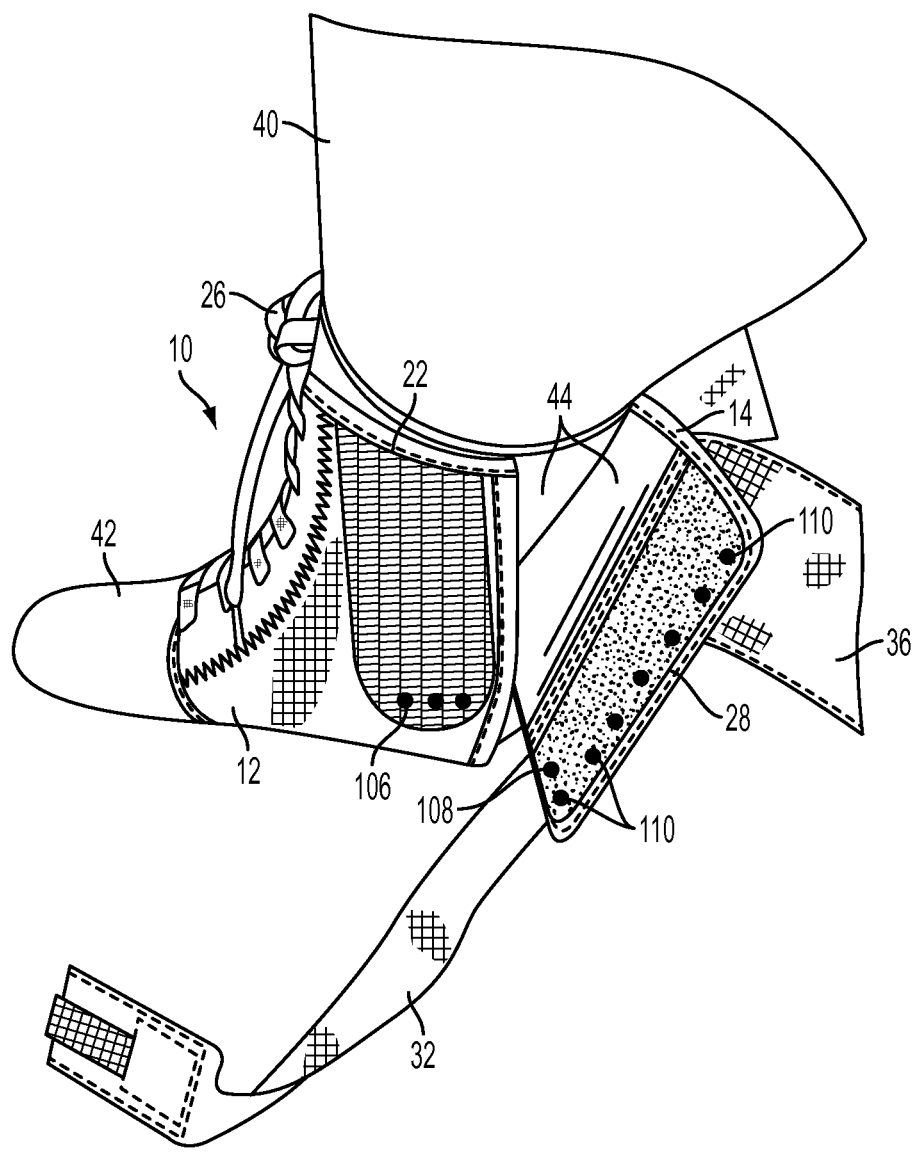
FIG. 15 shows an alternative embodiment ankle brace with eyelets to receive laces therethrough.
Figure 17:
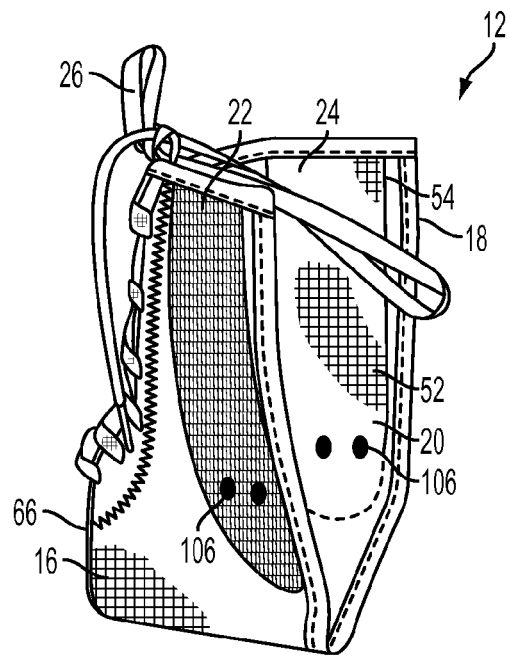
FIG. 17 shows an alternative embodiment ankle brace with eyelets to receive laces.

FIG. 15 shows eyelets 110 formed into the side panels 28, 30 of the rear portion 14. The eyelets 110 receive the laces 102 from the secondary closure 101 and may replace the lace loops 104 of FIG. 16 or be used in combination with them. FIG. 17 shows an alternative embodiment foot and ankle holder 12 with complementary attachment means 106 that are in the form of eyelets. Not shown are the complementary laces that are threaded through the eyelets to attach the foot and ankle holder 12 to the rear portion 14 via their respective side panels 22, 24, 28, 30.

Figure 18:
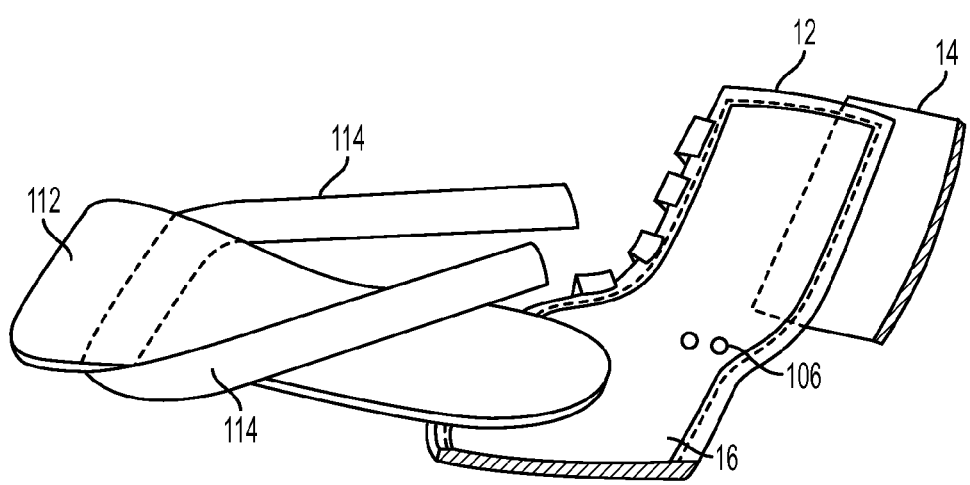
FIG. 18 shows an alternative embodiment ankle brace in a cross-sectional view taken across the sagittal plane with a foot plate.

FIG. 18 shows a preferred embodiment foot plate 112 to be located in the foot gauntlet or foot portion 16 of the foot and ankle holder 12, which is shown in cross-section along with the rear portion 14. The foot plate 112 is preferably made from a semi-rigid plastic sheet, a rubber sheet, or a more rigid metal sheet having a general silhouette of the sole of the patient's foot, or may be a partial silhouette thereof such as the forefoot or heel. The foot plate may have contours such as a raised arch area, or ribbing or stippling on its surface, as with a shoe insole. Because the foot plate 112 has some rigidity, it provides additional support of the patient's foot not contained by the foot and ankle holder 12. The foot plate 112 may be used in combination with or in lieu of the rigid heel support 76 shown in FIG. 12.

One or more straps 114 with hook and loop fasteners are stitched, glued, attached, or molded into the foot plate 112. To apply, the patient first places his or her foot on the foot plate 112, then inserts the foot into the foot and ankle holder 12 and uses the straps 114 to attach the foot plate 112 to the foot and ankle holder 112, encloses the ankle with the rear portion 14, and makes the final adjustments.

Unless otherwise described herein, conventional materials and manufacturing methods may be used to make the present invention. Additionally, various modifications may be made to the present invention without departing from the scope thereof. Although individual features of embodiments of the invention may be shown in some of the drawings and not in others, those skilled in the art will recognize that individual features of one embodiment of the invention can be combined with any or all of the features of another embodiment.

We claim:

1. A rear-, medial-, or lateral-entry ankle brace, comprising:
    a foot and ankle holder including a non-rigid fabric having a foot portion transitioning to an upper ankle portion with opposite first and second sides, wherein the upper ankle portion includes an open back, and a rear portion disposed on the upper ankle portion to at least partially enclose the open back, the rear portion at least having first and second panels that removably attach to the first and second sides of the upper ankle portion, respectively;
    means for binding the first and second sides of the upper ankle portion together;
    wherein one of the panels of the rear portion is independently detachable from the respective first and second sides of the upper ankle portion for rear, medial, and lateral entry;
    wherein the ankle brace further includes a secondary closure disposed on the first and second panels of the rear portion and at least partially overlying the means for binding; and
    wherein the first and second sides of the upper ankle portion engage the first and second panels of the rear portion via complementary attachment means.

2. The ankle brace of claim 1, wherein the ankle brace includes at least one elongated support strap connected to the holder to extend under the foot portion and then to extend generally upwardly and rearwardly for removable retention to one of the first and second sides of the upper ankle portion.

3. The ankle brace of claim 1, wherein the non-rigid fabric includes semi-rigid inserts embedded therein.

4. The ankle brace of claim 1, wherein the ankle brace includes a rigid foot plate disposed at the foot portion, wherein the rigid foot plate includes surface contours.

5. The ankle brace of claim 1, wherein the means for binding includes a plurality of loops extending from the first and second sides of the upper ankle portion and a lace passing through the loops.

6. The ankle brace of claim 1, wherein the means for binding includes a strap with hook and loop fasteners extending from one of the first and second sides of the upper ankle portion to the other.

7. The ankle brace of claim 1, wherein the secondary closure includes laces with attachment pads at ends of the laces.

8. The ankle brace of claim 1, wherein the complementary attachment means includes a plurality of receiving bosses and a pushbutton snap to engage at least one the receiving bosses.

9. A rear-, medial-, or lateral-entry ankle brace, comprising:
    a foot and ankle holder including a flexible fabric structure, defined by a foot portion transitioning to an upper ankle portion with opposite first and second sides, wherein the upper ankle portion includes an open front and an open back;
    a rear portion disposed on the upper ankle portion to at least partially enclose the open back, the rear portion having opposite first and second panels that removably attach to the first and second sides of the upper ankle portion, respectively;
    a tongue disposed at the open front of the upper ankle portion;
    a heel support strip disposed in the foot portion;
    means for binding disposed at the open front of the upper ankle portion to bind the first and second sides of the upper ankle portion together;
    at least one elongated support strap connected to the foot and ankle holder that extends under the foot portion and upwardly and rearwardly for removable retention to one of the first and second sides of the upper ankle portion;
    at least one elastic retention strap connected to the foot and ankle holder, and stretched around the holder;
    wherein the first and second panels are disposed on the respective first and second sides of the upper ankle portion for rear, medial, and lateral access; and
    wherein the first and second sides of the upper ankle portion engage the first and second panels of the rear portion via complementary attachment means.

10. The ankle brace of claim 9, wherein the ankle brace further comprises a secondary closure disposed on the first and second panels of the rear portion and at least partially overlying the means for binding.

11. The ankle brace of claim 10, wherein the secondary closure includes laces with attachment pads at opposite ends of the laces, and each pad includes hook and loop fasteners.

12. The ankle brace of claim 9, wherein the complementary attachment means include at least one of button snaps, zippers, rivets, screws, hooks and D-rings, hook and loop fasteners, and eyelets and laces.

13. The ankle brace of claim 9, wherein the ankle brace further comprises a semi-rigid foot plate with an attachment strap disposed in the foot portion.

14. A method of applying an orthopedic support to a person's foot, comprising:
    providing a foot and ankle holder including a flexible fabric, the holder defined by a foot portion transitioning to an upper ankle portion with first and second sides and an open back;
    providing a rear portion having side panels that independently, detachably attach to the first and second sides of the upper ankle portion and at least partially enclosing the open back;
    providing a means for binding to the secure the first and second sides of the upper ankle portion together;
    detaching one rear portion side panel from one of the respective first and second sides of the upper ankle portion to create a side opening;
    inserting the foot through the side opening; and
    re-attaching the one rear portion side panel to the one of the respective first and second sides.

15. The method of claim 14, wherein the method further comprises:
    moving the detached one rear portion side panel farther away from one of the respective first and second sides of the upper ankle portion to create a rear opening at the open back;
    inserting the foot through rear opening at the open back; and
    re-attaching the one rear portion side panel to the one of the respective first and second sides.

16. The method of claim 14, wherein the method further comprises:
    detaching one rear portion side panel from the first side of the upper ankle portion to create a rear opening in the open back;
    detaching another rear portion side panel from the second side of the upper ankle portion to create a larger rear opening from the rear opening in the open back;
    inserting the foot through the larger rear opening; and
    re-attaching the rear portion side panels to the first and second sides.

* * * * *